(12) United States Patent
Tsujita

(10) Patent No.: US 9,247,922 B2
(45) Date of Patent: Feb. 2, 2016

(54) ULTRASONIC DIAGNOSTIC APPARATUS AND ULTRASONIC IMAGE DISPLAY METHOD

(75) Inventor: Takehiro Tsujita, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 0 days.

(21) Appl. No.: 13/513,371

(22) PCT Filed: Nov. 25, 2010

(86) PCT No.: PCT/JP2010/070965
§ 371 (c)(1),
(2), (4) Date: Jun. 18, 2012

(87) PCT Pub. No.: WO2011/086774
PCT Pub. Date: Jul. 21, 2011

(65) Prior Publication Data
US 2012/0259223 A1     Oct. 11, 2012

(30) Foreign Application Priority Data

Jan. 18, 2010 (JP) .................. 2010-007699

(51) Int. Cl.
*A61B 8/08* (2006.01)
*A61B 8/00* (2006.01)
*G01S 7/52* (2006.01)
*G06T 15/08* (2011.01)
*G01S 15/89* (2006.01)

(52) U.S. Cl.
CPC . *A61B 8/08* (2013.01); *A61B 8/463* (2013.01); *A61B 8/466* (2013.01); *A61B 8/483* (2013.01); *A61B 8/485* (2013.01); *A61B 8/5223* (2013.01); *G01S 7/52071* (2013.01); *G06T 15/08* (2013.01); *G01S 7/52073* (2013.01); *G01S 15/8993* (2013.01)

(58) Field of Classification Search
CPC .......... A61B 8/08; A61B 8/463; A61B 8/466; A61B 8/483; A61B 8/485; A61B 8/5223; G01S 15/8993; G01S 7/52071; G01S 7/52073; G06T 15/08
USPC .......................... 600/437, 438, 442; 382/128
See application file for complete search history.

(56) References Cited

U.S. PATENT DOCUMENTS 5,720,291 A * 2/1998 Schwartz ...................... 600/456
6,083,162 A * 7/2000 Vining ........................... 600/407
(Continued)

FOREIGN PATENT DOCUMENTS

JP    A-H10-507954    8/1998
JP    A-2001-014446   1/2001
(Continued)

OTHER PUBLICATIONS

Sep. 2, 2014 Notice of Grounds for Rejection issued in Japanese Patent Application No. 2011-549868 (with English translation).
(Continued)

*Primary Examiner* — Katherine Fernandez
(74) *Attorney, Agent, or Firm* — Oliff PLC

(57) ABSTRACT

Provided is an ultrasonic diagnostic apparatus configured to appropriately display a region of interest that is intended to be observed in a 3-dimensional elastic image, and also provided is an ultrasonic image display method. The ultrasonic diagnostic apparatus includes an elastic opacity table creating section for creating, on the basis of the elasticity values, an elastic opacity table used for setting an opacity in the volume rendering of the elastic volume data.

21 Claims, 10 Drawing Sheets

(56) References Cited

U.S. PATENT DOCUMENTS

| | | |
|---|---|---|
| 6,480,732 B1 | 11/2002 | Tanaka et al. |
| 2006/0229513 A1* | 10/2006 | Wakai .......................... 600/407 |
| 2006/0241458 A1 | 10/2006 | Hayashi et al. |
| 2007/0038104 A1 | 2/2007 | Hyun |
| 2007/0112270 A1* | 5/2007 | Waki et al. ................... 600/455 |
| 2009/0096807 A1* | 4/2009 | Silverstein et al. ........... 345/593 |

FOREIGN PATENT DOCUMENTS

| | | |
|---|---|---|
| JP | A-2007-007402 | 1/2007 |
| JP | A-2007-044231 | 2/2007 |
| JP | A-2007-117384 | 5/2007 |
| JP | A-2007-125169 | 5/2007 |
| JP | A-2008-259605 | 10/2008 |
| WO | WO 2005/006987 A1 | 1/2005 |
| WO | WO 2005/048847 A1 | 6/2005 |
| WO | WO 2009/001077 A2 | 12/2008 |

OTHER PUBLICATIONS

Mar. 5, 2014 First Office Action issued in Chinese Patent Application No. 201080061672.3 with partial English-language translation.

Dec. 28, 2010 International Search Report issued in International Patent Application No. PCT/JP2010/070965.

\* cited by examiner

ULTRASONIC DIAGNOSTIC APPARATUS AND ULTRASONIC IMAGE DISPLAY METHOD

FIELD OF THE INVENTION

The present invention relates to an ultrasonic diagnostic apparatus and an ultrasonic image display method capable of displaying a 3-dimensional elastic image showing the hardness or softness of biological tissue in an object using ultrasonic waves.

DESCRIPTION OF RELATED ART

An ultrasonic diagnostic apparatus transmits ultrasonic waves to the inside of an object to be examined by an ultrasonic probe, and is capable of obtaining and displaying a 3-dimensional tomographic image and a 3-dimensional elastic image on the basis of the reception signals received from the biological tissue in the object.

At the time of superimposing and displaying a 3-dimensional elastic image over a 3-dimensional tomographic image, the opacity of the 3-dimensional tomographic image is set so that the profile or volume of the hard region or soft region in the 3-dimensional elastic image can be recognized (for example, Patent Document 1).

PRIOR ART DOCUMENTS

Patent Documents

Patent Document 1: JP-A-2008-259605

Though the technique disclosed in Patent Document 1 performs volume rendering of a 3-dimensional tomographic image based on an opacity table in which the opacity is defined in accordance with the feature quantity of an elasticity value, the setting of opacity in the volume rendering process of the 3-dimensional elastic image is not disclosed therein.

Therefore, there is a possibility, at the time of constructing a 3-dimensional elastic image by performing volume rendering in the line of sight, in the case that a thick region which is not a region of interest that exists in front of the region of interest in the line of sight, that the region of interest is hidden behind the region other than the region of interest. For example, in the setting of opacity that changes linearly from the hard region which is the region of interest to the soft region, there is a possibility that the hard region is hidden behind the region having the average hardness which is the region other than the region of interest.

The objective of the present invention is to provide the ultrasonic diagnostic apparatus and the ultrasonic image display method capable of appropriately displaying a desired region of interest in a 3-dimensional elastic image.

BRIEF SUMMARY OF THE INVENTION

In order to achieve the above-described objective, the ultrasonic diagnostic apparatus of the present invention comprises:

an ultrasonic probe provided with transducers configured to transmit and receive ultrasonic waves;

a transmission unit configured to transmit ultrasonic waves to an object to be examined via an ultrasonic probe;

a reception unit configured to receive the reflected echo signals from the objective;

a 3-dimensional elastic image constructing unit configured to construct a 3-dimensional elastic image by performing volume rendering on the elastic volume data formed by the elasticity values based on reflected echo signals; and a display unit configured to display an 3-dimensional elastic image, wherein the 3-dimensional elastic image constructing unit constructs a 3-dimensional elastic image by setting the opacity in the volume rendering of the elastic volume data on the basis of elasticity values.

In accordance with the present invention, it is possible to appropriately display a desired region of interest in a 3-dimensional elastic image.

DETAILED DESCRIPTION OF THE INVENTION

An ultrasonic diagnostic apparatus 100 to which the present invention is applied will be described referring to FIG. 1.

Figure 1:
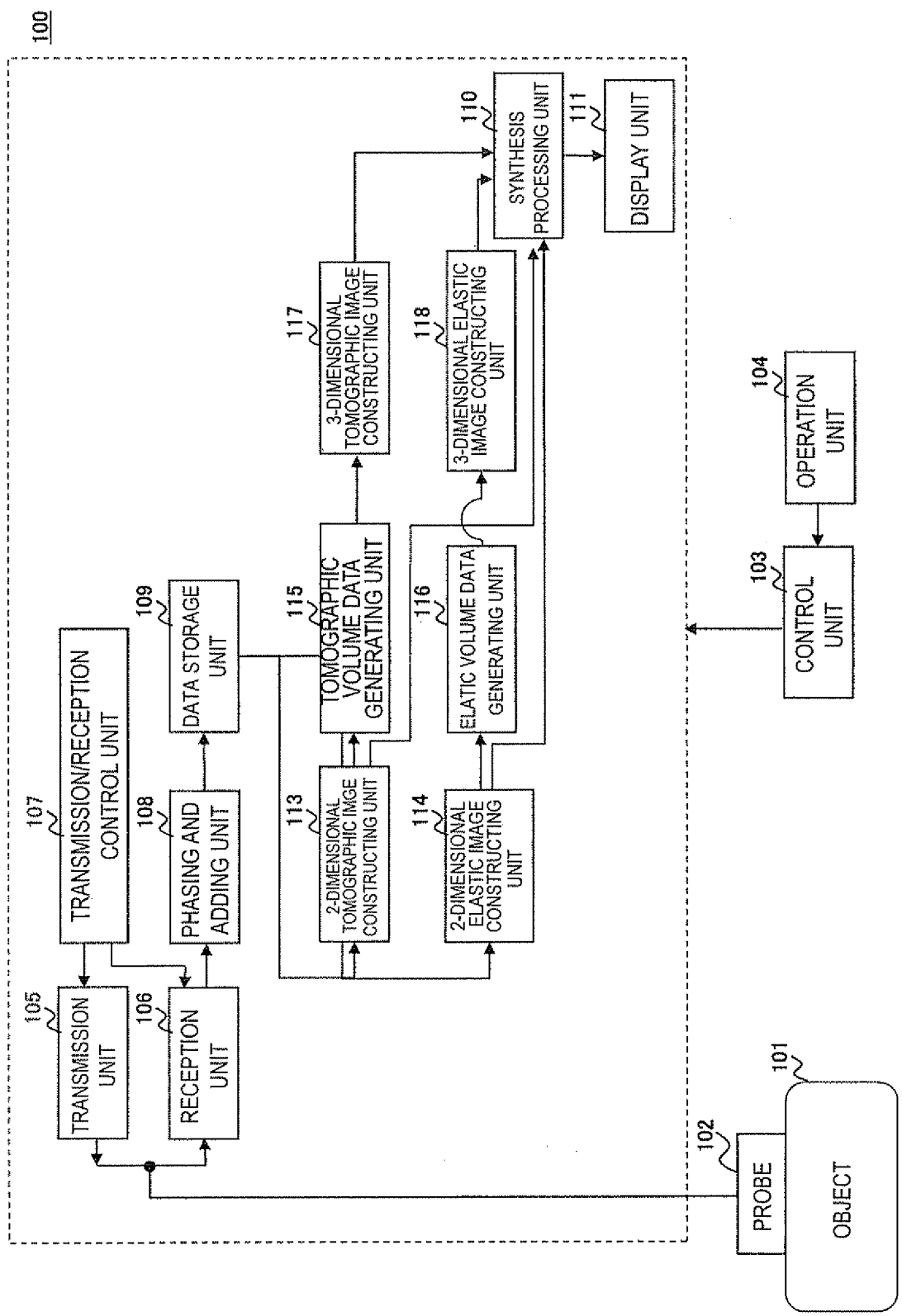
FIG. 1 is a block diagram showing the general configuration of the present invention.

As shown in FIG. 1, the ultrasonic diagnostic apparatus 100 comprises an ultrasonic probe 102 configured to be used by applying to an object 101, a transmission unit 105 configured to repeatedly transmit ultrasonic waves to the object 101 via the ultrasonic probe 102 at predetermined time intervals, a reception unit 106 configured to receive the reflected echo signals reflected from the object 101, a transmission/reception control unit 107 configured to control the transmission unit 105 and the reception unit 106, and a phasing and adding unit 108 configured to perform phasing and adding on the reflected echoes received by the reception unit 106.

The ultrasonic probe 102 is formed by a plurality of transducers arrayed therein, and has a function to transmit/receive ultrasonic waves to the object via the transducers. The ultrasonic probe 102 is formed by a plurality of rectangle or fan-shaped transducers, capable of transmitting/receiving ultrasonic waves 3-dimensionally by mechanically vibrating the transducers in the direction orthogonal to the array direction of the plurality of transducers. The ultrasonic probe 102 may also be provided with a plurality of transducers being 2-dimensionally arrayed therein and a function capable of electronically controlling transmission and reception of ultrasonic waves.

The transmission unit 105 generates a transmission pulse for generating an ultrasonic wave by activating transducers of the ultrasonic probe 102. The transmission unit 105 has a function to set the convergent point of a transmitted ultrasonic wave at a certain depth. Also, the reception unit 106 generates an RF signal, i.e. a reception signal by amplifying the reflected echo signal received by the ultrasonic probe 102 at a predetermined gain. The ultrasonic transmission/reception control unit 107 controls the transmission unit 105 and the reception unit 106.

The phasing and adding unit 108 controls the phase of the RF signal which is amplified in the reception unit 106 and generates RF signal frame data (equivalent to RAW data) by forming an ultrasonic beam with respect to one or plural convergent points.

Further, the ultrasonic diagnostic apparatus 100 comprises a data storage unit 109 configured to store the RF signal frame data generated in the phasing and adding unit 108, a 2-dimensional tomographic image constructing unit 113 configured to construct a 2-dimensional tomographic image on the basis of the RF signal frame data stored in the data storage unit 109, a tomographic volume data generating unit 115 configured to generate tomographic volume data by performing 3-dimensional coordinate conversion on the 2-dimensional tomographic image constructed by the 2-dimensional tomographic image constructing unit 113 on the basis of the position where the 2-dimensional tomographic image is obtained, a 3-dimensional tomographic image constructing unit 117 configured to construct a 3-dimensional tomographic image from tomographic volume data, a 2-dimensional elastic image constructing unit 114 configured to construct a 2-dimensional elastic image on the basis of the plural sets of RF signal frame data stored in the data storage unit 109, an elastic volume data generating unit 116 configured to generate elastic volume data by performing 3-dimensional coordinate conversion on the 2-dimensional elastic image constructed in the 2-dimensional elastic image constructing unit 114 on the basis of the position where the 2-dimensional elastic image is obtained, a 3-dimensional elastic image constructing unit 118 configured to construct a 3-dimensional elastic image from the elastic volume data on which the coordinate conversion is performed, a synthesis processing unit 110 configured to synthesize a 2-dimensional tomographic image and a 2-dimensional elastic image or a 3-dimensional tomographic image and a 3-dimensional elastic image, and a display unit 111 configured to display images such as a synthetic image which is synthesized by the synthesis processing unit 110, a 2-dimensional tomographic image or a 2-dimensional tomographic image.

Also, the ultrasonic diagnostic apparatus 100 comprises a control unit 103 configured to control the above-described components and an operation unit 104 configured to perform various input to the control unit 103. The operation unit 104 comprises devices such as a keyboard or a trackball.

The 2-dimensional tomographic image constructing unit 113 executes signal processing such as gain compensation, log compression, detection, edge enhancement or filtering by inputting the RF signal frame data output from the data storage unit 109 on the basis of the setting condition in the control unit 103, and constructs a 2-dimensional tomographic image.

The ultrasonic probe 2 is capable of measuring the transmission/reception directions (θ, φ) at the time of transmitting and receiving ultrasonic waves, and the tomographic volume data generating unit 115 generates the tomographic volume data by executing 3-dimensional conversion on plural 2-dimensional tomographic images on the basis of the transmission/reception directions (θ, φ) which are equivalent to the positions where the 2-dimensional images are obtained.

The 3-dimensional tomographic image constructing unit 117 performs volume rendering on the basis of the luminance and the opacity of the tomographic volume data. In concrete terms, the 3-dimensional tomographic image constructing unit 117 is configured by a tomogrpahic opacity table creating section 200 and a tomographic rendering calculation section 202 as shown in FIG. 2(a).

The tomographic opacity table creating section 200 creates a tomographic opacity table in which the luminance of a tomographic image represented by voxel values is set as the lateral axis and the opacity is set as the vertical axis. The tomographic rendering calculation section 202 performs volume rendering on the basis of the created tomographic opacity table using the following equation for constructing a 3-dimensional tomographic image from the tomographic volume data.

[Equation 1]

$$C\text{out}(i) = C\text{out}(i-1) + (a - A\text{out}(i-1)) \cdot A(i) \cdot C(i) \cdot S(i) \quad (1)$$

$$A\text{out}(i) = A\text{out}(i-1) + (1 - A\text{out}(i-1)) \cdot A(i) \quad (2)$$

$$A(i) = \text{Opacity}[C(i)] \quad (3)$$

$C(i)$ is the luminance value of the i-th voxel that exists on the line of sight when a 3-dimensional tomographic image is viewed from a certain point on the created 2-dimensional projected plane. $C\text{out}(i)$ is the output pixel value. For example, when luminance values of N-number of voxels are lined up on the line of sight, the luminance value $C\text{out}(N-1)$ obtained by integration from $i=0$ to $N-1$ is the pixel value to be ultimately output. $C\text{out}(i-1)$ represents the integrated value up to the $(i-1)$-th voxel.

Also, $A(i)$ is the opacity of the i-th luminance value that exists on the line of sight, and is the tomographic opacity table which takes the values of 0-1.0 as indicated in the above equation (3). The tomographic opacity table is generated in the tomographic opacity table creating section 200, and determines the contribution ratio on the output 2-dimensional projected plane (3-dimensional tomographic image) by referring to the opacity based on the luminance value.

$S(i)$ is the weighting component for shading to be computed by the slope which is acquired by luminance $C(i)$ and the surrounding pixel values thereof. For example, when the light source coincides with the normal line of the plane which is centered on voxel "i", 1.0 is given for the maximum reflection, and when the light source and the normal line are orthogonal to each other, 0.0 is given which indicates accentuation effect.

Both $C\text{out}(i)$ and $A\text{out}(i)$ have 0 as the initial value. As shown in the above equation (2), $A\text{out}(i)$ is integrated each time it passes through a voxel and converged to 1.0. Thus as shown in the above equation (1), when integrated value $A\text{out}(i-1)$ of up to the $(i-1)$-th opacity is about 1.0, the i-th and sequence luminance values $C(i)$ will not be reflected on the output image.

The tomographic opacity table creating section 200 is capable of imaging the tomographic volume data with high luminance without imaging the tomographic volume data with low luminance by, for example, setting the opacity of the low luminance value in the tomographic opacity table as zero. The tomographic rendering calculation section 202 perform volume rendering on the basis of the created tomographic opacity table, and outputs the constructed 3-dimensional tomographic image to the synthesis processing unit 110.

In the present embodiment, it is possible to make changes in a tomographic opacity table. By the control of the control unit 103 based on the operation of the operation unit 104, the tomographic opacity table creating section 200 can make changes in the tomographic opacity table, thereby the tomographic volume data in which the changes are made in accordance with the changed tomographic opacity table can be imaged.

The 2-dimensional elastic image constructing unit 114 measures the displacement from the plural sets of RF signal frame data stored in the data storage unit 109. Then the 2-dimensional elastic image constructing unit 114 calculates the elasticity value on the basis of the measured displacement, and constructs a 2-dimensional elastic image. The elasticity value includes elasticity information such as the strain, elasticity modulus, displacement, viscosity or strain ratio.

The elastic volume data generating unit 116 executes 3-dimensional conversion on plural 2-dimensional elastic images on the basis of the transmission/reception directions ($\theta$, $\phi$) equivalent to the positions where the 2-dimensional elastic images are obtained, and generates the elastic volume data. On the elastic volume data, color values (blue, light blue, green, yellow, red, etc.) are allotted in accordance with the elasticity values. For example, a hard region is colored in blue and a soft region is colored in red.

Figure 2:
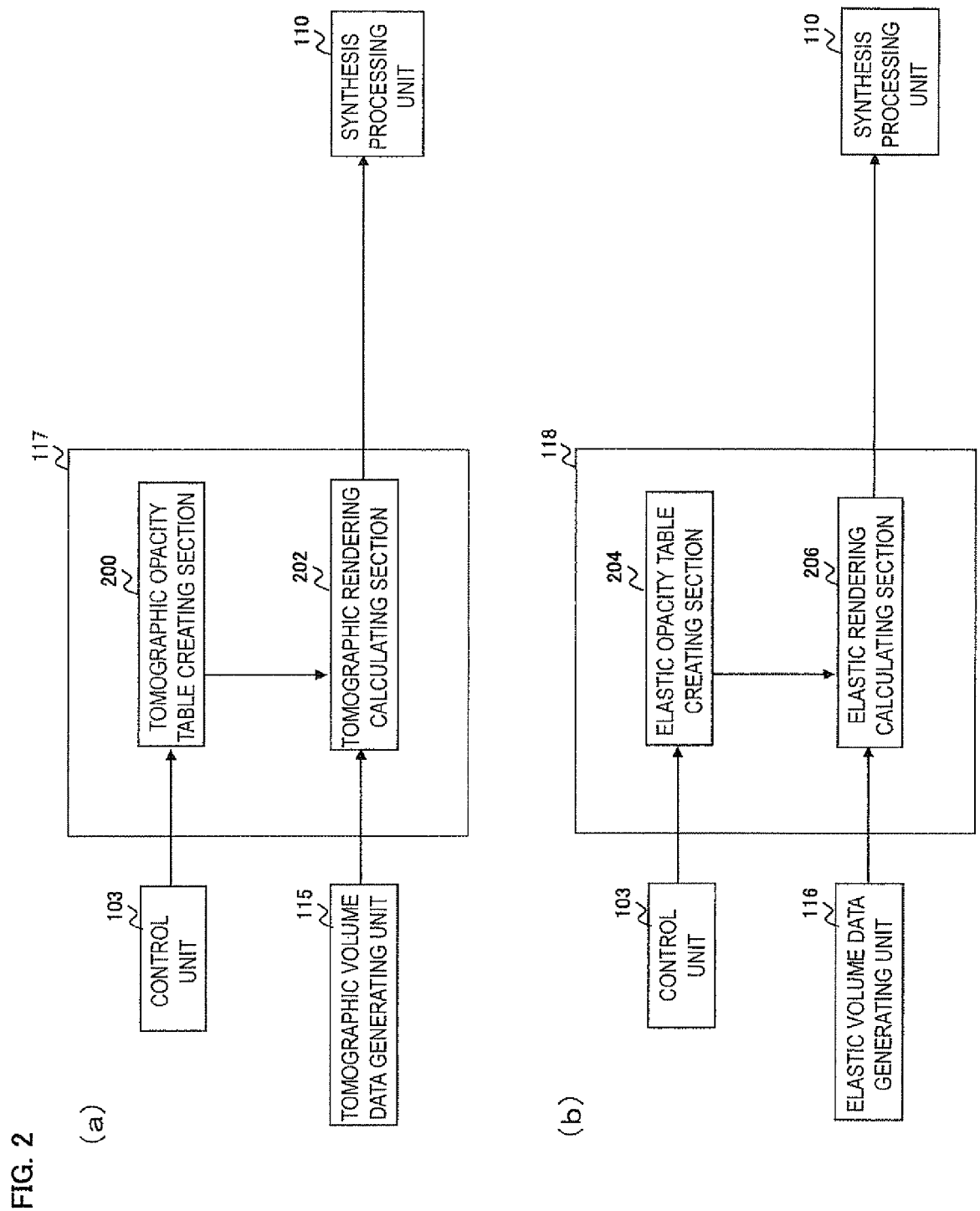
FIG. 2 is a view showing a 3-dimensional tomographic image constructing unit 117 and a 3-dimensional elastic image constructing unit 118 of the present invention.

The 3-dimensional elastic image constructing unit 118 constructs a 3-dimensional elastic image by setting the opacity in volume rendering of the elastic volume data on the basis of the elasticity values. The opacity is set by the elastic opacity table in which the relationship between the opacity and the elasticity value is set. In concrete terms, the 3-dimensional elastic image constructing unit 118 is configured by an elastic opacity table creating section 204 and an elastic rendering calculation section 206 as shown in FIG. 2(*b*).

Figure 3:
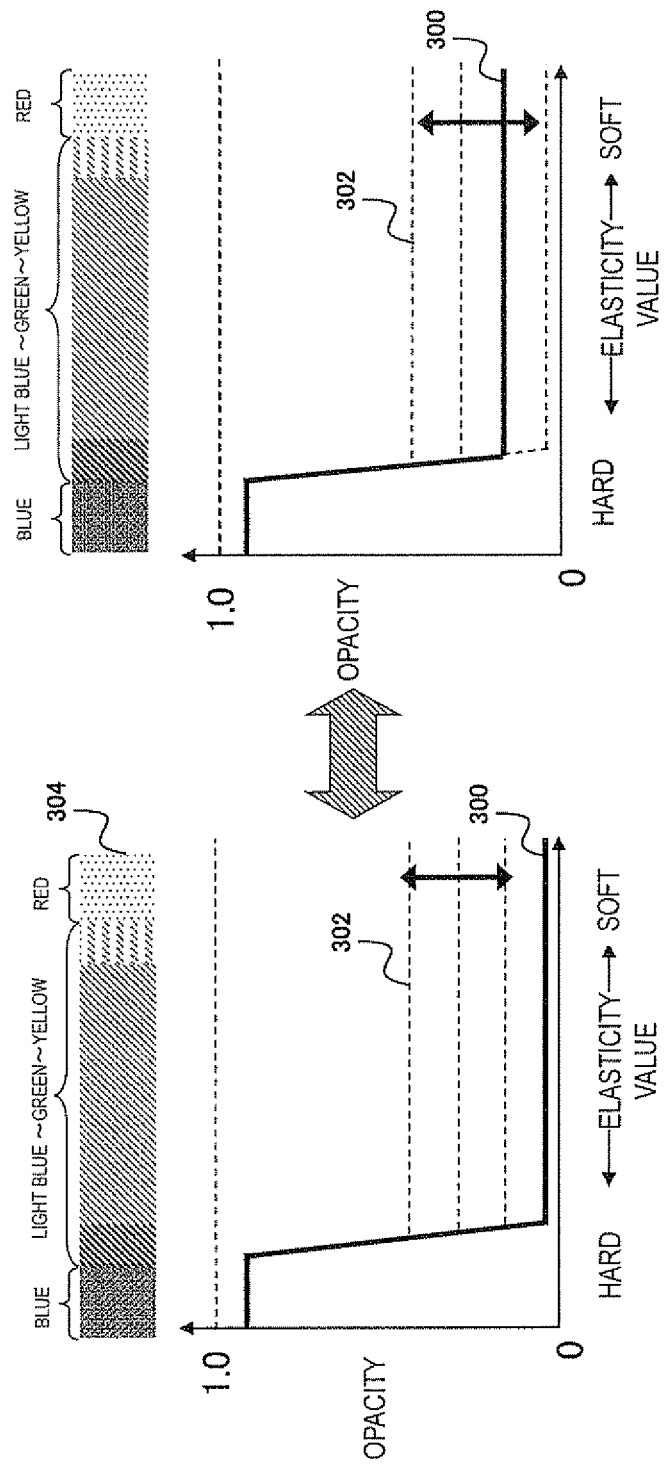
FIG. 3 shows an example of an elastic opacity table in a first embodiment of the present invention.
Figure 4:
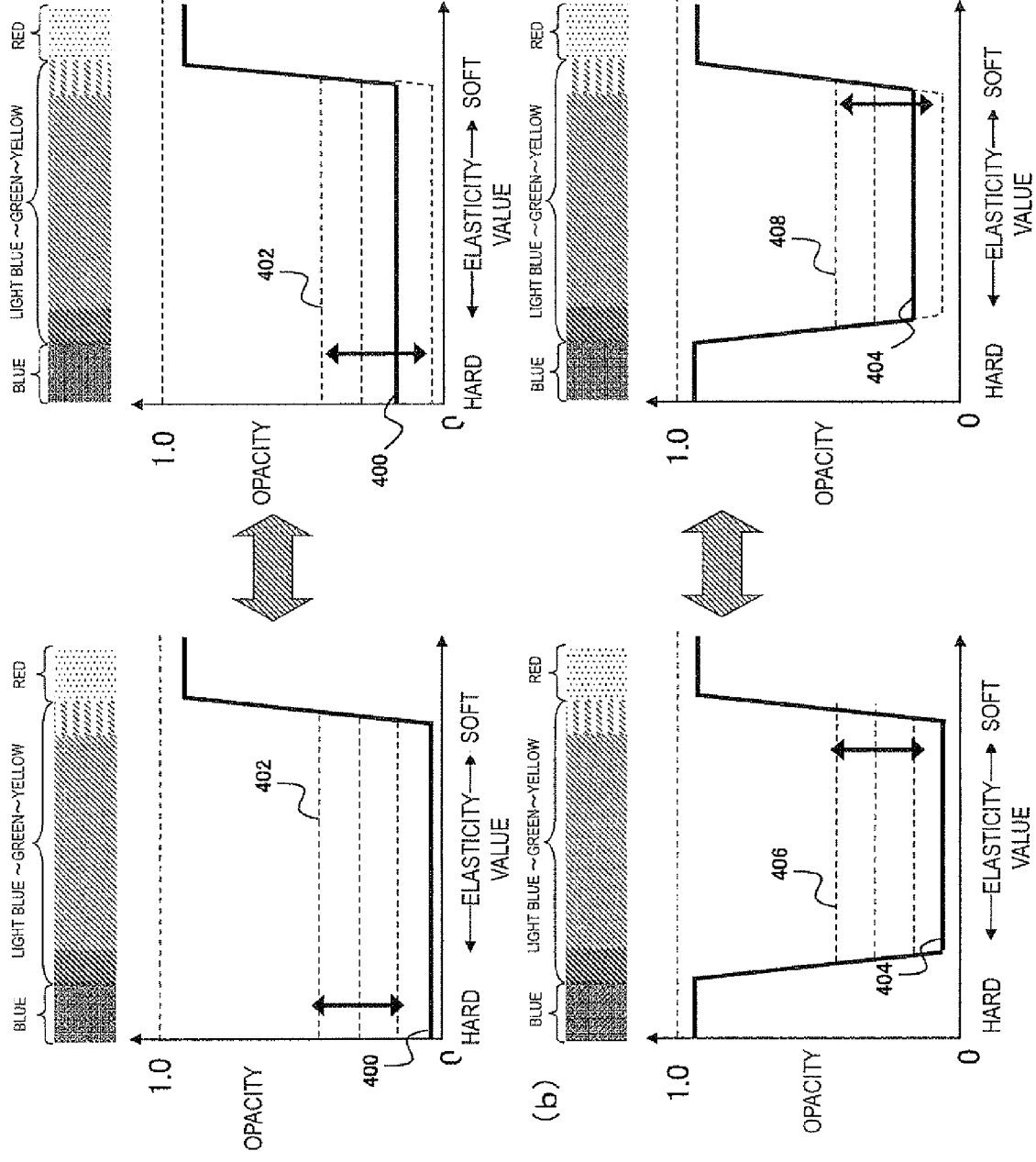
FIG. 4 shows an example of the elastic opacity table in the first embodiment of the present invention.

The elastic opacity table creating section 204 creates the elastic opacity table in which the relationship between the opacity and the elasticity value is set. The elastic opacity table is created for setting the opacity in the volume rendering on the basis of the elasticity value. FIG. 3 and FIG. 4 show the elastic opacity table to be created by the elastic opacity table creating section 204. The relationship between the elasticity value and the opacity is determined by the elastic opacity table, and the contribution ratio of the elastic volume data is set on the 2-dimensional projected plane in the display unit 111.

The elastic opacity table is formed by an opacity line 300 for setting the opacity on the basis of the elasticity value and a guideline 302 for guiding the setting of the opacity line 300. Also, a color bar 304 which corresponds to the elasticity value of the opacity table is displayed on FIG. 3 and FIG. 4.

As shown in FIG. 3, the elastic opacity table is set by the opacity line 300 to emphasize and display the region of interest (hard region) to which blue color is given based on the elasticity value. The opacity is set by the opacity line 300 so that the opacity of the region of interest (hard region) determined by the elasticity value becomes higher compared to the opacity of the region other than the region of interest (standard region, soft region) to which green color or red color is given. The standard region to be the region other than the region of interest has the average hardness in the elastic volume data, to which mainly green color is given. The region other than the region of interest mainly includes the standard region.

In the elastic opacity table, when the opacity in the opacity line 300 of the region of interest (hard region) to which blue color is given is set as T1, T1 is set at a value which is close to 1.0 (for example, $0.7 \leq T1 < 1.0$). Also, when the opacity in the opacity line 300 of the region other than the region of interest (standard region, soft region) to which green or red is given is set as T2, T2 is set at a value which is close to 0 (for example, $0 < T2 \leq 0.5$). The opacity of the opacity line 300 is set so that opacity T2 of the region other than the region of interest will not be zero. The purpose of this setting is to display the region of interest (hard region) to which blue color is given relatively. Also, when the opacity in the opacity line 300 of the region between the region of interest to which light blue is given and the region other than the region of interest is set as T3, it is set at a value between T2 and T1 (for example, $T2 \leq T3 \leq T1$)

In the present embodiment, further changes can be made in the opacity of the elastic opacity table. The opacity of the elastic opacity table can be changed by the elastic opacity table creating section 204 under the control of the control unit 104 based on the operation in the operation unit 104.

The elastic opacity table creating section 204 makes changes in the opacity of the opacity line 300 which is equivalent to the region (the region including the standard region) other than the region of interest to which green color, etc. is given.

In concrete terms, when an operator moves the opacity line 300 set in the region other than the region of interest shown in the left view of FIG. 3 in the upward direction, the elastic opacity table creating section 204 sets the opacity of the elastic opacity table so that the opacity of the region other than the region of interest is at the higher level as shown in the right view of FIG. 3. Conversely, when the operator moves the opacity line 300 set in the region other than the region of interest in the downward direction, the elastic opacity table creating section 204 sets the opacity of the elastic opacity table so that the opacity of the region other than the region of interest is at the lower level. The guideline 302 for guiding the setting of the opacity line 300 indicates the movable range of the opacity line 300 (for example, $0 < T2 \leq 0.5$). In this manner, the operator can set the opacity in the opacity line 300 to be set at the region other than the region of interest (hard region).

While the opacity line 300 is represented by a straight line in the present embodiment, it may also be represented by a curved line. In the case that the opacity line 300 is represented by a curved line, the elastic opacity table creating section 204 sets the opacity corresponding to the curved line in the region (the region which includes the standard region) other than the region of interest.

The elastic rendering calculation section 206 performs volume rendering using the elastic opacity table based on the opacity line 300 created in the elastic opacity table creating section 204 and the following equation.

[Equation 2]

$$E_{out}(i) = E_{out}(i-1) + (1 - A_{out}(i-1)) \cdot A(i) \cdot E(i) \cdot S(i) \quad (4)$$

$$A_{out}(i) = A_{out}(i-1) + (1 - A_{out}(i-1)) \cdot A(i) \quad (5)$$

$$A(i) = \text{Opacity}[E(i)] \quad (6)$$

E(i) is the i-th elasticity value that exists on the line of sight in the case that a 3-dimensional elastic image is viewed from a certain point on the created 2-dimensional projected plane. Eout(i) is the output pixel value. For example, when elasticity values of N-voxels are lined up in the line of sight, integrated value Eout(N−1) in which the elasticity values of i=0-N−1 are integrated is the pixel value to be ultimately output. Eout(i−1) represents the integrated value up to the (i−1)-th voxel. Also, A(i) is the opacity of the i-th elasticity value which exists in the line of sight, and is the elastic opacity table which is created in the elastic opacity table creating section 204 as shown in the equation (6).

S(i) is the weighting component for shading to be computed by the slope which is acquired based on elasticity value E(i) and the surrounding elasticity values thereof. For example, when the light source coincides with the normal line of the plane which is centered on voxel "i", 1.0 is given for the maximum reflection, and when the light source and the normal line are orthogonal to each other, 0.0 is given which indicates accentuation effect.

Both Eout(i) and Aout(i) have 0 as the initial value. As shown in the equation (5), Aout(1) is integrated each time it passes through a voxel and converged to 1.0. Thus as shown in the equation (4), when integrated value Aout(i−1) of the opacity of up to the (i−1)-th voxel is about 1.0, the i-th and subsequent voxel values E(i) will not be reflected on the output image.

The synthesis processing unit 110 respectively reads out the 3-dimensional tomographic image which is constructed as above and a 3-dimensional elastic image, performs cumulative addition by multiplying the transmission factor which is set in the operation unit 104 on a 2-dimensional projected plane, and creates a 3-dimensional synthetic image. The display unit 111 displays the 3-dimensional synthetic image created in the synthesis processing unit 110.

Also, the elastic opacity table creating section 204 is capable of setting the opacity by the opacity line 300 of the elastic opacity table so that the region of interest (soft region) to which red color is given based on the elasticity value is emphasized and displayed as shown in FIG. 4(*a*). The elastic opacity table is set such that the opacity of the region of interest determined by the elasticity value becomes higher compared to the opacity of the region other than the region of interest. In concrete terms, the opacity is set by the opacity line 300 so that the region of interest (soft region) determined on the basis of the elasticity value becomes higher compared to the opacity of the region other than the region of interest (standard region, hard region) to which green color or blue color, etc. is given.

The elastic opacity table creating section 204 is capable of setting the opacity of an opacity line 400 which is equivalent to the region other than the region of interest (standard region, hard region) to which green color or red color, etc. is given under the control of the control unit 103 based on the operation of the operation unit 104. When the opacity line 400 set at the region other than the region of interest is moved in the upward direction as shown in the left view of FIG. 4(*a*), the opacity of the region other than the region of interest is set at the higher level as shown in the right view of FIG. 4(*a*). Conversely, when the opacity line 400 set at the region other than the region of interest is moved in the downward direction, the opacity of the region other than the region of interest is set at the lower level. A guideline 402 for guiding the setting of the opacity line 400 indicates the movable range of the opacity line 400 (for example, 0<T2≤0.5)

Also, the elastic opacity table creating section 204 is capable of setting the opacity by an opacity line 404 of the elastic opacity table such that the region of interest (hard region, soft region) to which blue color or red color is given on the basis of the elasticity value is emphasized and displayed as shown in FIG. 4(*b*). The opacity is set by the opacity line 404 so that the region of interest (hard region, soft region) determined by the elasticity value becomes higher compared to the opacity of the region other than the region of interest (standard region) to which green color, etc. is given.

The elastic opacity table creating section 204 is capable of setting the opacity of the opacity line 404 which is equivalent to the region other than the region of interest (standard region) to which green color, etc. is given, under control of the control unit 103 based on the operation of the operation unit 104. When the opacity line 404 set at the region other than the region of interest shown in the left view of FIG. 4(*b*) is moved in the upward direction, the opacity of the region other than the region of interest is set at the higher level as shown in the right view of FIG. 4(*b*). Conversely, when the opacity line 404 set at the region other than the region of interest is moved in the downward direction, the opacity of the region other than the region of interest is set at the lower level. A guideline 406 for guiding the setting of the opacity line 404 indicates the movable range of the opacity line 404 (for example, 0<T2≤0.5).

Figure 5:
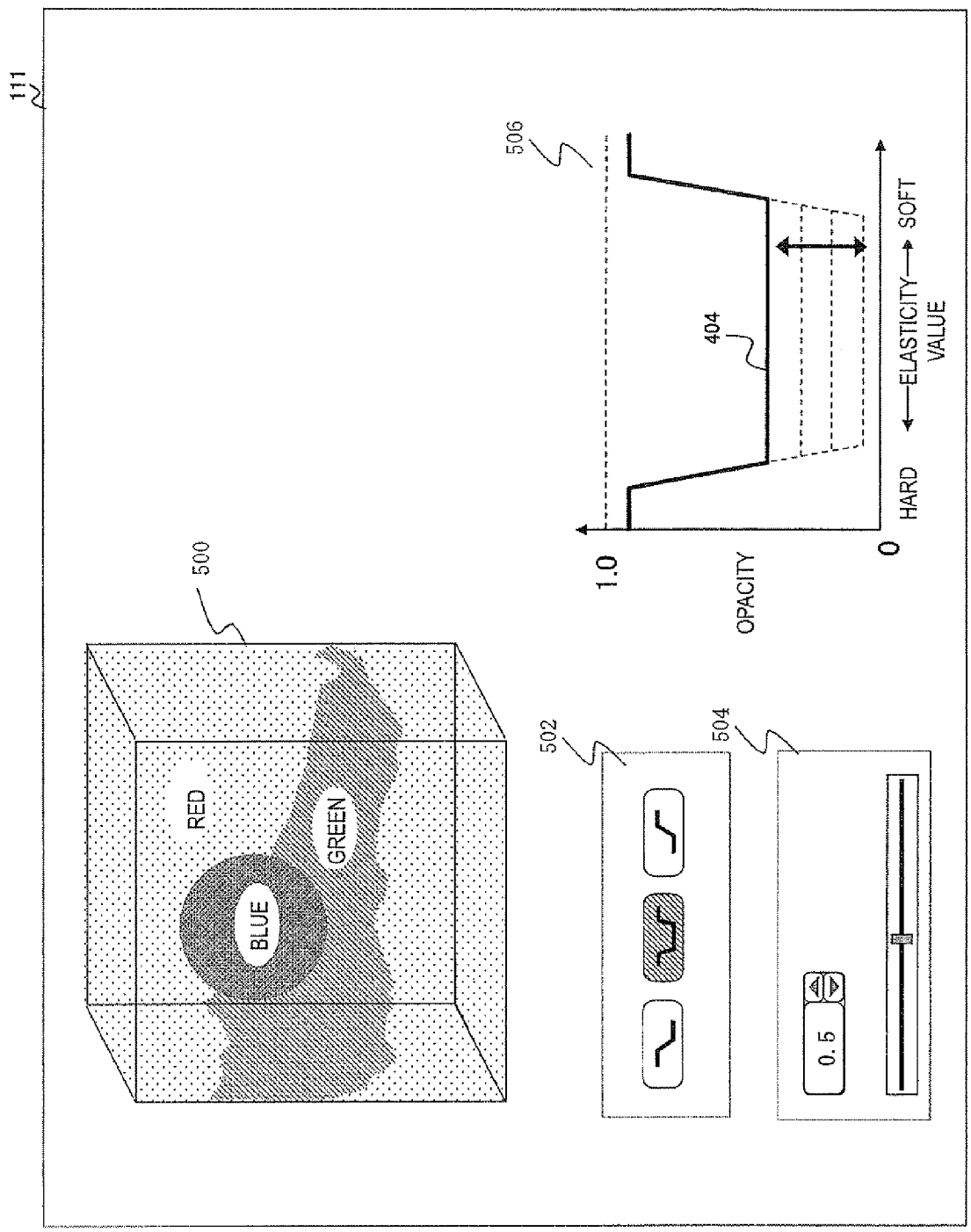
FIG. 5 shows a display pattern of a display unit 111 related to the present invention.

FIG. 5 shows a display pattern of the display unit 111. An image 500, an opacity table selecting area 502, an opacity setting area 504 and an elastic opacity table 506 are displayed on the same screen.

The image 500 is, for example a 3-dimensional synthetic image in which a 3-dimensional tomographic image and a 3-dimensional elastic image are synthesized, or a 3-dimensional elastic image.

The opacity table selecting area 502 is for selecting the elastic opacity table from among a plurality of opacity tables which are stored in advance. It comprises a storage area (not shown in the diagram) that stores a plurality of elastic opacity tables in FIG. 3, FIGS. 4(*a*) and (*b*) that are described above. A plurality of opacity tables are displayed on the display unit 111, and an elastic opacity table can be selected under control of the control unit 103 based on the operation of the operation unit 104. The elastic opacity table 506 which is selected by the operation unit 104 is displayed. Here, the concaved elastic opacity table in FIG. 4(*b*) is selected, and is displayed as shown in 506.

The opacity setting area 504 is capable of setting the opacity of the opacity line 404 which is equivalent to the region other than the region of interest (standard region) by a numeric setting unit or a slide bar which is equivalent to the operation unit 104. Here, the opacity of the opacity line 404 is set at "0.5". The numeric or the slide bar can also indicate the settable range of the opacity of the opacity line 400.

Since the image 500, the opacity table selecting area 502, the opacity setting area 504 and the opacity table are displayed on the same screen, the operator can select the pattern of the opacity table or set the opacity of the elastic opacity table while observing the image 500, for constructing an optimum image.

As described above, in accordance with the first embodiment, at the time of constructing a 3-dimensional elastic image by performing volume rendering in the line of sight direction, even when a thick region (the region including the standard region) other than the region of interest exists in front of the region of interest which is the observation target in the line of sight of the 3-dimensional elastic image, the region of interest can be displayed without being hidden by the region (the region including the standard region) other than the region of interest by setting the opacity of an elastic opacity table in accordance with the elasticity value.

For example, in the case that the region of interest is at the deep portion in the line of sight, the region of interest can be observed by lowering the opacity of the region (the region including the standard region) other than the region of interest to make the region (the region including the standard region) other than the region of interest which is on the near side of the region of interest transparent.

In this manner, a region of interest which is the observation target in a 3-dimensional elastic image can be appropriately displayed.

Here, the second embodiment will be described referring to FIG. 1~FIG. 6. The difference from the first embodiment is that the opacity of the region excluding the standard region is set by the elastic opacity table creating section 204. The configuration other than the elastic opacity table creating section 204 will be omitted since it is the same as the first embodiment.

Figure 6:
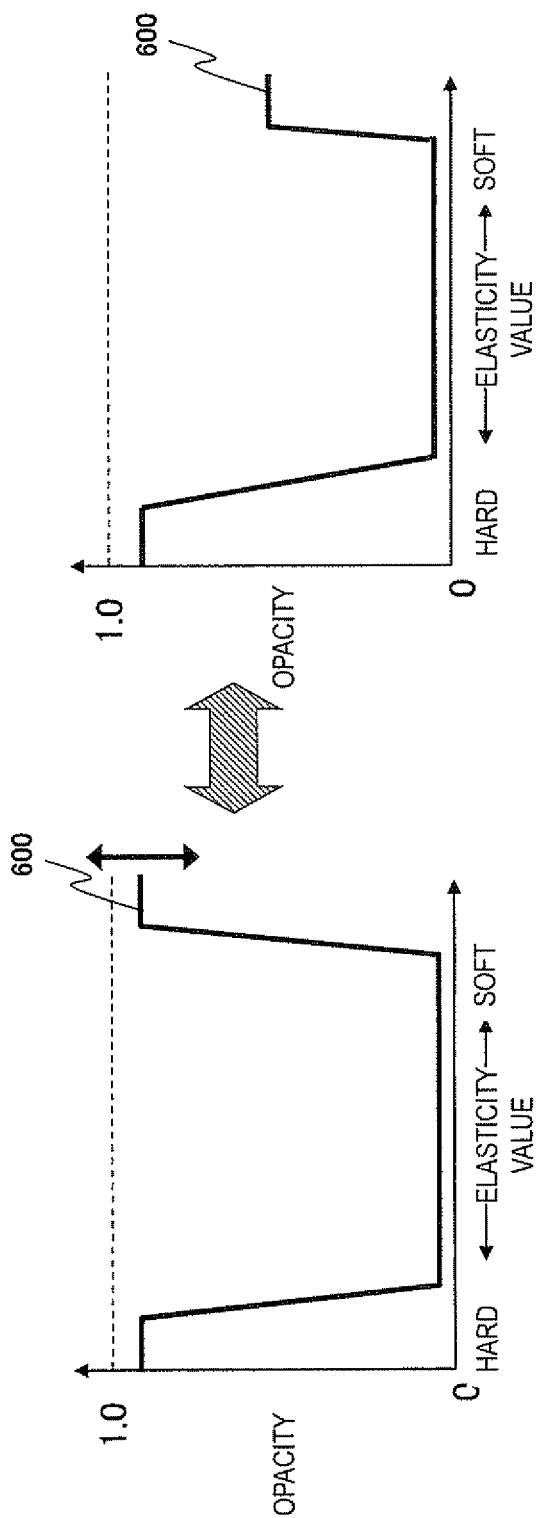
FIG. 6 shows an example of the elastic opacity table in a second embodiment of the present invention.

The elastic opacity table creating section 204 sets the opacity by an opacity line 600 of an elastic opacity table so that the region of interest (hard region, soft region) to which blue color or red color is given on the basis of the elasticity value is emphasized and displayed, as shown in the left view of FIG. 6.

Given this factor, for example in the case that the region of interest (hard region) to which blue color is given is to be further emphasized, the elastic opacity table creating section 204 sets the opacity of the opacity line 600 which is equivalent to the region excluding the standard region to which red color is given. In concrete terms, when the opacity line 600 which is set at the opacity of the region excluding the standard region shown in the left view of FIG. 6 is moved in downward direction, the opacity of the region excluding the standard region is set lower as shown in the right view of FIG. 6.

In the present embodiment in the case that the region of interest (soft region) to which red color is given is to be further emphasized, the elastic opacity table creating section 204 can also set the opacity of the opacity line 600 which is equivalent to the region excluding the standard region to which blue color is given.

As described above, in accordance with the present embodiment at the time of constructing a 3-dimensional elastic image by performing volume rendering in the line of sight direction, it is possible to further emphasize and display the region of interest which requires specific attention.

The third embodiment will be described referring to FIG. 1~FIG. 8. The difference from the first embodiment and the second embodiment is that the opacity of the elastic opacity table is set for every line of sight (direction) on the basis of the number of voxels in the elastic volume data on which volume rendering is performed. In other words, the opacity in the elastic opacity table is set on the basis of the number of voxels in the elastic volume data on which volume rendering is performed.

Figure 7:
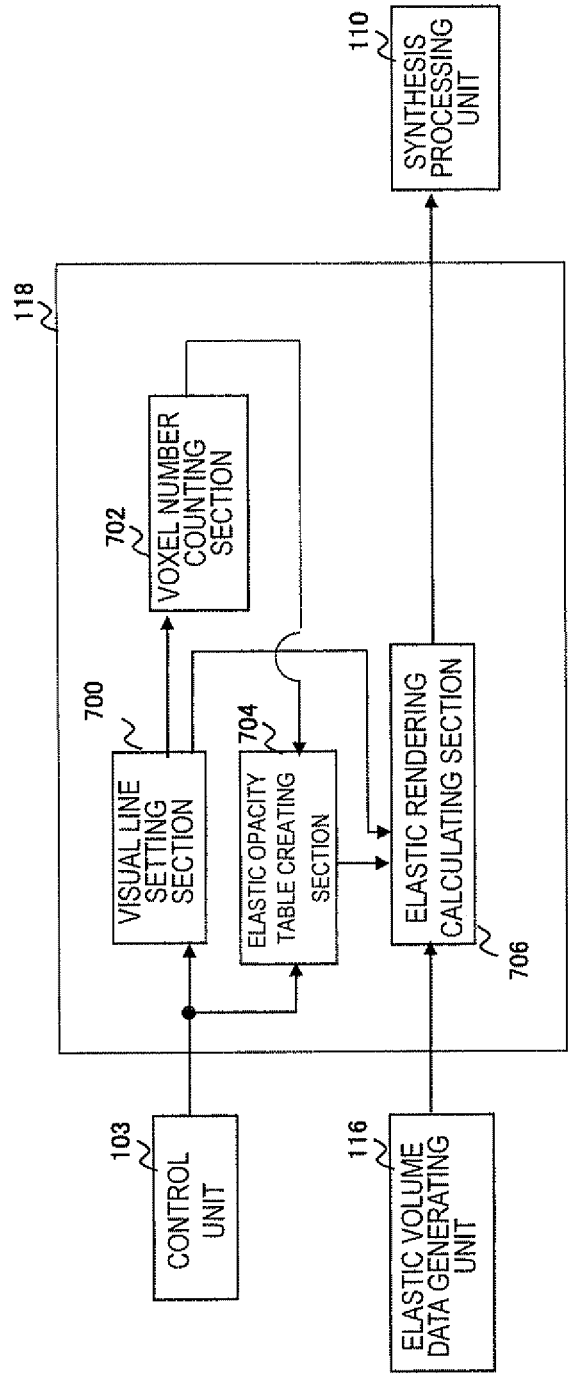
FIG. 7 is a view showing the 3-dimensional elastic image constructing unit 118 in a third embodiment of the present invention.

As shown in FIG. 7, the 3-dimensional elastic image constructing unit 118 is formed by a visual-line setting section 700 configured to set the line of sight (direction) with respect to the elastic volume data, a voxel counting section 702 configured to count the number of voxels in the line of sight (direction) set in the elastic volume data, an elastic opacity table creating section 704 configured to create the elastic opacity table based on the counted number of voxels, and an elastic rendering calculation section 706 configured to perform volume rendering on the elastic volume data using the created elastic opacity table.

Figure 8:
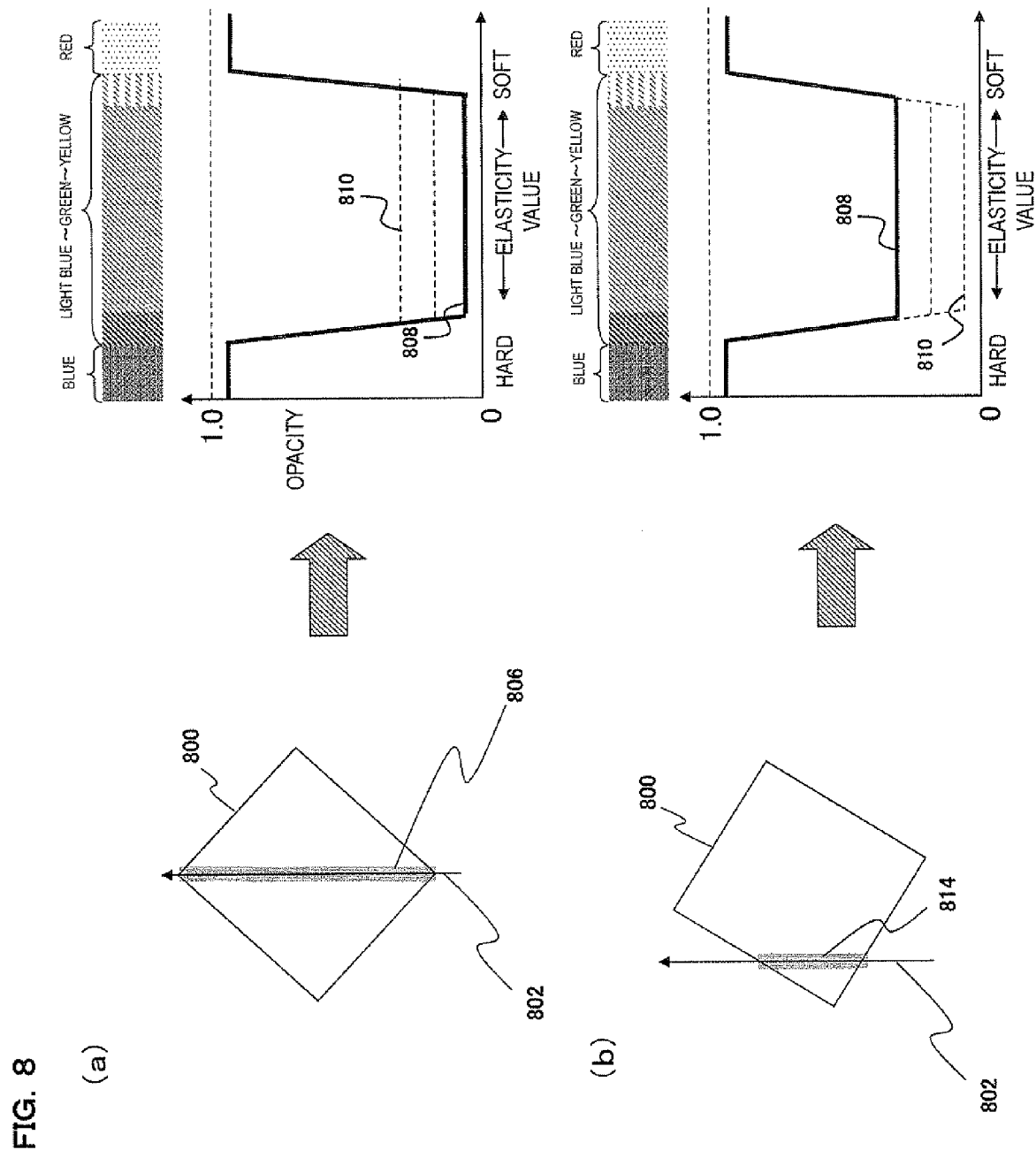
FIG. 8 shows an example of the elastic opacity table in the third embodiment of the present invention.

The 3-dimensional elastic image constructing unit 118 in the present embodiment will be described in concrete terms referring to FIG. 8. In the pattern of FIG. 8(a), the visual-line setting section 700 sets a line of sight 802 on the diagonal line of elastic volume data 800 under control of the control unit 103 based on the operation of the operation unit 104. The display unit 111 can display the elasticity volume data 800 and the line of sight 802. The voxel counting section 702 counts the number of voxels in the line of sight 802 which is set in the elastic volume data 800. The counted number of voxels is indicated by the length of a line 806. The voxel counting section 702 may also execute the processing for searching a structural object that positions at the shallowest or deepest portion in the line of sight and calculate the number of voxels up to the target structural object.

As shown in the first embodiment, the elastic opacity table creating section 704 first sets the opacity of the elastic opacity table by an opacity line 808 so that the opacity of the region of interest (hard region, soft region) to which blue color or red color that are determined by the elasticity value is given becomes higher compared to the opacity of the region other than the region of interest (standard region) to which green color, etc. is given.

In the pattern of FIG. 8(a), since the line of sight 802 is set on the diagonal line of the elastic volume data 800, it has the maximum number of voxels for performing volume rendering. Given this factor, the elastic opacity creating section 704 sets the opacity of the elastic opacity table in accordance with the number of voxels, so that the region of interest (hard region, soft region) will not be hidden by the region other than the region of interest (standard region) due to having higher number of voxels for performing volume rendering.

In concrete terms, the elastic opacity table creating section 704, when the opacity in the opacity line 808 of the region other than the region of interest (standard region) to which green color is given is set as T2, sets the opacity line 808 so that an opacity T2 of the region other than the region of interest becomes low (for example, 0<T2≤0.1). A guideline 810 is for indicating the movable range of the opacity line 808 (for example, 0<T2≤0.5).

The elastic rendering calculation section 706 performs volume rendering using the elastic opacity table based on the opacity line 808 created in the elastic opacity table creating section 704 and the above equation (equation 2).

On the other hand, in the pattern of FIG. 8(b), the visual-line setting section 700 sets the line of sight 802 so that the line of sight 802 will not cross orthogonally with respect to a side of the elastic volume data 800, under control of the control unit 103 based on the operation of the operation unit 104. The voxel counting section 702 counts the number of voxels in the line of sight 802 which is set in the elastic volume data 800. The counted number of voxels is indicated by the length of a line 814.

As in the first embodiment, the elastic opacity table creating section 704 first sets the opacity of the elastic opacity table by the opacity line 808 so that the opacity of the region of interest (hard region, soft region) to which blue color or red color determined by the elasticity is given becomes higher compared to the opacity of the region other than the region of interest (standard region) to which green color, etc. is given.

In the pattern of FIG. 8(b), since the line of sight 802 is set so that the line of sight 802 will not cross a side of the elastic volume data 800 orthogonally, the number of voxels for performing volume rendering is smaller than the pattern in FIG. 8(a). The elastic opacity creating section 704 sets the opacity of the elastic opacity table in accordance with the number of voxels, so that the region of interest (hard region, soft region) will not be hidden by the region other than the region of interest (standard region).

In concrete terms, the elastic opacity table creating section 704, when the opacity in the opacity line 808 of the region other than the region of interest (standard region) to which green color is given is set as T2, sets the opacity line 808 so that an opacity T2 of the region other than the region of interest becomes high (for example, 0.1<T2≤0.3).

The elastic rendering calculation section 706 performs volume rendering using the elastic opacity table based on the opacity line 808 created in the elastic opacity table creating section 704 and the above equation (equation 2).

In the third embodiment, when the number of voxels for performing volume rendering is high, the elastic opacity table creating section 704 sets the opacity line 808 so that the opacity of the region other than the region of interest becomes low. On the other hand, when the number of voxels for performing volume rendering is low, the elastic opacity table creating section 704 sets the opacity line 808 so that the opacity of the region other than the region of interest becomes high. In this manner, even when a 3-dimensional elastic image is constructed by changing the line of sight (direction), since the elastic opacity table creating section 704 counts the number of voxels for each line of sight and arbitrarily sets the opacity in accordance with the number of voxels for each line of sight (direction), it is possible to display a 3-dimensional elastic image evenly from any line of sight (direction).

The fourth embodiment will be described referring to FIGS. 1~10. The difference between the present embodiment and the first-third embodiments is that the cumulative opacity of the elastic volume data in the line of sight (direction) is analyzed and the opacity of the elastic opacity table is set on the basis of the analyzed cumulative opacity.

Figure 9:
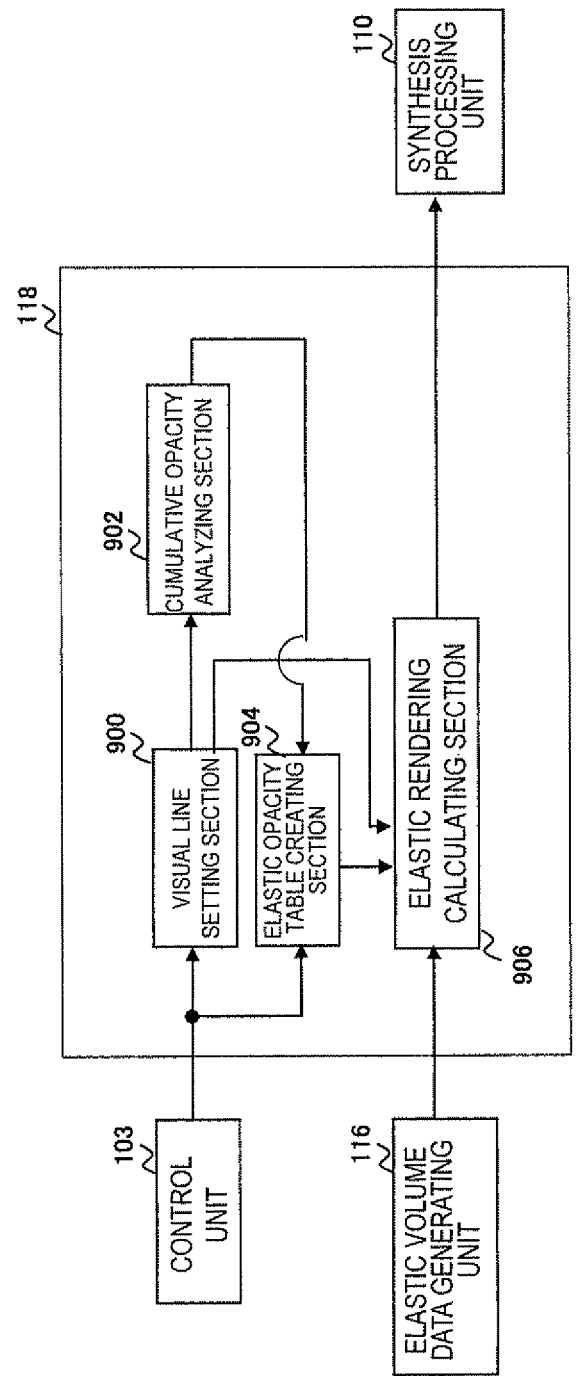
FIG. 9 is a view showing the 3-dimensional elastic image constructing unit 118 in a fourth embodiment of the present invention.

As shown in FIG. 9, the 3-dimensional elastic image constructing unit 118 is formed by a visual-line setting section 900 configured to set the line of sight (direction) with respect to the elastic volume data, a cumulative opacity analyzing section 902 configured to analyze the cumulative opacity with respect to the distance of the line of sight (number of voxels) in the set line of sight (direction), an elastic opacity table creating section 904 configured to create an elastic opacity table on the basis of the analyzed cumulative opacity, and an elastic rendering calculation section 906 configured to perform volume rendering of the elastic volume data using the created elastic opacity table.

Figure 10:
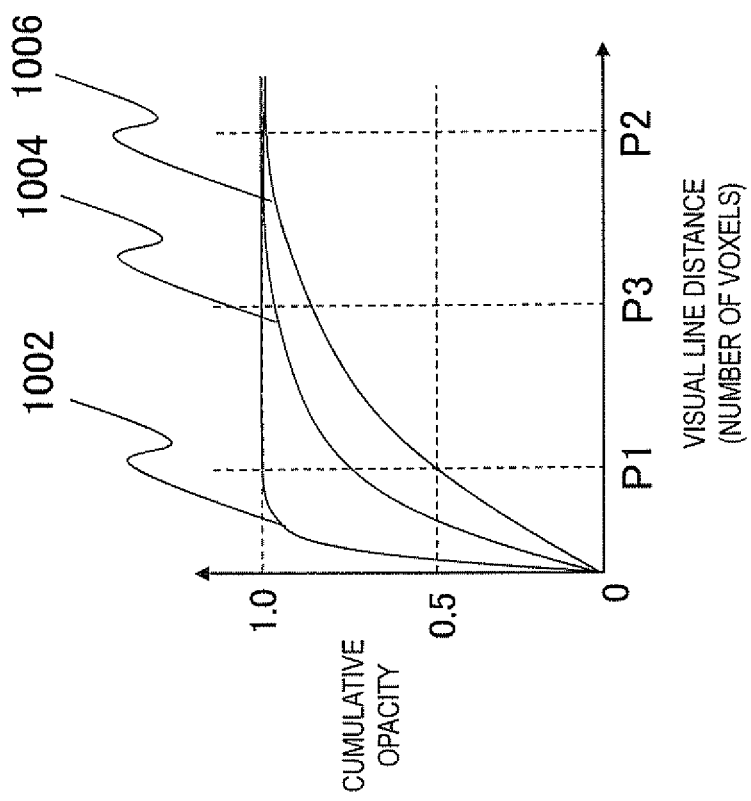
FIG. 10 shows an example of the elastic opacity table in the fourth embodiment of the present invention.

The 3-dimensional elastic image constructing unit 118 in the present embodiment will be described in concrete terms referring to FIG. 10. FIG. 10 shows the cumulative opacity with respect to the distance of the line of sight (number of voxels) in the line of sight (direction) set in the visual-line setting section 900. In the present embodiment, a cumulative opacity graph 1004 is set as optimal cumulative opacity graph, since the setting of the opacity thereof is generally well-balanced.

The cumulative opacity analyzing section 902 analyzes the cumulative opacity with respect to the visual-line distance (number of voxels) in the set line of sight (direction).

Here, it is assumed that a cumulative opacity graph 1002 is acquired as a result of analyzing the cumulative opacity in the line of sight (direction) in the cumulative opacity analyzing section 902. The cumulative opacity graph 1002 has a high cumulative opacity with respect to the visual-line distance (number of voxels), and the cumulative opacity reaches 1.0 at the point where the visual-line distance (number of voxels) reaches P1.

Given this factor, the elastic opacity table creating section 904 sets the opacity in the elastic opacity table so that the cumulative opacity graph 1002 in the line of sight (direction) becomes the optimal cumulative opacity graph 1004. In concrete terms, elastic opacity table creating section 904, for example moves the opacity line 404 which is set in the region other than the region of interest to which green color, etc. is given in the downward direction, and lowers the opacity of the region other than the region of interest as shown in FIG. 4(b).

Also, it is assumed that a cumulative opacity graph 1006 is acquired as a result of analyzing the cumulative opacity in the line of sight (direction) by the cumulative opacity analyzing section 902. The cumulative opacity of the cumulative opacity graph 1006 with respect to the visual-line distance (number of voxels) is low, and the cumulative opacity reaches 1.0 at the point where the visual-line distance (number of voxels) reaches P2. Also, the cumulative opacity of the cumulative opacity graph 1006 reaches 0.5 at the position of a visual-line distance (number of voxels) P1. In this case, the output elasticity value becomes half the elasticity value of the elastic volume data, and the value can be diagnosed as harder than the actual hardness.

Given this factor, the elasticity opacity table creating section 904 sets the opacity in the elasticity opacity table so that the cumulative opacity graph 1006 in the line of sight (direction) becomes the optimal cumulative opacity graph 1004. In concrete terms, for example the elastic opacity table creating section 904 moves the opacity line 404 which is set at the region other than the region of interest to which green color, etc. is given toward upward direction, and sets the opacity at a higher value than the opacity in the region other than the region of interest, as shown in FIG. 4(b)

The elastic rendering calculation unit 906 performs volume rendering using the elasticity opacity table created in the elastic opacity table creating section 904 the above equation (equation 2).

In the fourth embodiment, a 3-dimensional elastic image can be displayed evenly from any line of sight (direction), by analyzing the cumulative opacity in the line of sight (direction) and setting the opacity of the elastic opacity table on the basis of the analyzed cumulative opacity.

DESCRIPTION OF REFERENCE NUMERALS

100 ultrasonic diagnostic apparatus
102 ultrasonic probe
103 control unit
104 operation unit
105 transmission unit
106 reception unit
107 transmission/reception control unit
108 phasing and adding unit
109 data storage unit
110 synthesis processing unit
111 display unit
113 2-dimensional tomographic image constructing unit
115 elastic image 3-dimensional coordinate converting unit
117 3-dimensional tomographic image constructing unit
114 2-dimensional elastic image constructing unit
116 elastic image 3-dimensional coordinate converting unit
118 3-dimensional elastic image constructing unit

The invention claimed is:
1. An ultrasonic diagnostic apparatus comprising:
an ultrasonic probe provided with transducers for transmitting/receiving ultrasonic waves;
a transmission unit configured to transmit the ultrasonic waves to an object to be examined via the ultrasonic probe;
a reception unit configured to receive reflected echo signals from the object;

a processor configured to act as:

a 3-dimensional elastic image constructing unit configured to construct a 3-dimensional elastic image comprising a region of interest and a region other than the region of interest by performing volume rendering on elastic volume data formed by elasticity values based on the reflected echo signals;

an elastic opacity table creating section configured to create an elastic opacity table setting a relationship between an opacity in the volume rendering of the elastic volume data and an elasticity value, the region of interest having a first opacity corresponding to a first elasticity value range in the elastic opacity table, and the region other than the region of interest having a second opacity corresponding to a second elasticity value range in the elastic opacity table, the second elasticity value range being a larger range than the first elasticity value range, the elastic opacity table creating section configured to set the first opacity of the region of interest higher than the second opacity of the region other than the region of interest; and a display unit configured to display the 3-dimensional elastic image and an opacity setting area for setting an opacity of the region other than the region of interest relative to the first opacity of the region of interest in accordance with operation by an operator, wherein the elastic opacity table creating section is configured to, in response to the operation by the operator on the opacity setting area, change the second opacity to a third opacity corresponding to the second elasticity value range in the elastic opacity table, and the 3-dimensional elastic image constructing unit is configured to set an opacity of the 3-dimensional elastic image depicting the region of interest and the region other than the region of interest using the elastic opacity table.

2. The ultrasonic diagnostic apparatus according to claim 1, wherein the display unit is configured to display, in addition to the 3-dimensional elastic image and the opacity setting area, the elastic opacity table.

3. The ultrasonic diagnostic apparatus according to claim 1, further comprising a 3-dimensional tomographic image constructing unit configured to generate tomographic volume data based on the reflected echo signals and perform volume rendering based on a luminance and an opacity of the tomographic volume data, wherein the display unit is further configured to display a 3-dimensional tomographic image.

4. An ultrasonic diagnostic apparatus comprising:

an ultrasound probe provided with transducers for transmitting/receiving ultrasonic waves;

a transmission unit configured to transmit the ultrasonic waves to an object to be examined via the ultrasonic probe;

a reception unit configured to receive reflected echo signals from the object;

a processor configured to act as:

a 3-dimensional elastic image constructing unit configured to construct a 3-dimensional elastic image comprising a region of interest and a region other than the region of interest by performing volume rendering on elastic volume data formed by elasticity values based on the reflected echo signals;

an opacity table selecting area configured to enable an operator to select one of a plurality of tables that are stored in advance, each of the plurality of tables setting a different predetermined relationship between an opacity in the volume rendering of the elastic volume data and an elasticity value, wherein the selected one of the plurality of tables serves as an elastic opacity table used to set an opacity of the region other than the region of interest relative to an opacity of the region of interest in accordance with operation by an operator, the region of interest having a given opacity in the selected one of the plurality of tables, wherein the opacity of the region of interest is set higher than the opacity of the region other than the region of interest in each of the plurality of tables; and a display unit configured to display the 3-dimensional elastic image and the opacity table selecting area, wherein the 3-dimensional elastic image constructing unit is configured to set an opacity of the 3-dimensional elastic image depicting the region of interest and the region other than the region of interest using the elastic opacity table.

5. The ultrasonic diagnostic apparatus according to claim 4, wherein the display unit is configured to display, in addition to the 3-dimensional elastic image and the opacity table selecting area, the elastic opacity table.

6. The ultrasonic diagnostic apparatus according to claim 4, wherein the elastic opacity table is formed by an opacity line for setting the opacity in accordance with the elasticity values.

7. The ultrasonic diagnostic apparatus according to claim 4, further comprising a 3-dimensional tomographic image constructing unit configured to generate tomographic volume data based on the reflected echo signals and perform volume rendering based on a luminance and an opacity of the tomographic volume data, wherein the display unit is further configured to display a 3-dimensional tomographic image.

8. An ultrasonic diagnostic apparatus comprising:

an ultrasonic probe provided with transducers for transmitting/receiving ultrasonic waves;

a transmission unit configured to transmit the ultrasonic waves to an object to be examined via the ultrasonic probe;

a reception unit configured to receive reflected echo signals from the object;

a processor configured to act as a 3-dimensional elastic image constructing unit configured to construct a 3-dimensional elastic image by performing volume rendering on elastic volume data formed by elasticity values based on the reflected echo signals:

the processor further configured to act as a voxel counting section configured to count a total number of voxels corresponding to a length of a line of sight within a region on which the volume rendering is performed for each line-of-sight direction of the elastic volume data on which the volume rendering is performed, the processor is further configured to act as an elastic opacity table creating section configured to create an elastic opacity table and configured to set an opacity with respect to a region other than a region of interest in the elastic opacity table according to an inverse relationship with the total number of voxels counted for each line-of-sight direction, wherein the opacity with respect to the region other than the region of interest is decreased as the total number of voxels counted for each line-of-sight direction increases, and the opacity with respect to the region other than the region of interest is increased as the total number of voxels counted for each line-of-sight direction decreases; and a display configured to display the 3-dimensional elastic image; wherein the 3-dimensional elastic image constructing unit is configured to, based on the elasticity values, set an opacity of the 3-dimensional elastic image using the elastic opacity table, wherein in the elastic opacity table a relationship between an opacity value and an elasticity value is set.

9. The ultrasonic diagnostic apparatus according to claim 8, wherein the elastic opacity table is set so that the region of interest has an opacity higher than the opacity of the region other than the region of interest.

10. The ultrasonic diagnostic apparatus according to claim 8, further comprising a 3-dimensional tomographic image constructing unit configured to generate tomographic volume data based on the reflected echo signals and perform volume rendering based on a luminance and an opacity of the tomographic volume data, wherein the display unit is further configured to display a 3-dimensional tomographic image.

11. An ultrasonic diagnostic apparatus comprising:
an ultrasonic probe provided with transducers for transmitting/receiving ultrasonic waves;
a transmission unit configured to transmit ultrasonic waves to an object to be examined via the ultrasonic probe;
a reception unit configured to receive reflected echo signals from the object;
a processor configured to act as a 3-dimensional elastic image constructing unit configured to construct a 3-dimensional elastic image by performing volume rendering on elastic volume data formed by elasticity values based on the reflected echo signals;
the processor configured to act as a voxel counting section configured to execute processing for searching for a structural object, to which the volume rendering is performed, on a line of sight, and count a total number of voxels up to the structural object, the total number of voxels corresponding to the length of a line extending up to the structural object;
the processor is further configured to act as an elastic opacity table creating section configured to create an elastic opacity table and configured to set an opacity with respect to a region other than a region of interest in the elastic opacity table according to an inverse relationship with the total number of voxels counted for each line-of-sight direction, wherein the opacity with respect to the region other than the region of interest is decreased as the total number of voxels counted for each line-of-sight direction increases, and the opacity with respect to the region other than the region of interest is increased as the total number of voxels counted for each line-of-sight direction decreases; and
a display configured to display the 3-dimensional elastic image;
wherein
the 3-dimensional elastic image constructing unit is configured to, based on the elasticity values, set an opacity of the 3-dimensional elastic image using the elastic opacity table, wherein in the elastic opacity table a relationship between an opacity value and an elasticity value is set.

12. The ultrasonic diagnostic apparatus according to claim 11, wherein the elastic opacity table is set so that the region of interest has an opacity higher than the opacity of the region other than the region of interest.

13. The ultrasonic diagnostic apparatus according to claim 11, further comprising a 3-dimensional tomographic image constructing unit configured to generate tomographic volume data based on the reflected echo signals and perform volume rendering based on a luminance and an opacity of the tomographic volume data, wherein the display unit is further configured to display 3-dimensional tomographic image.

14. An ultrasonic diagnostic apparatus comprising:
an ultrasonic probe provided with transducers for transmitting/receiving ultrasonic waves;
a transmission unit configured to transmit ultrasonic waves to an object to be examined via the ultrasonic probe;
a reception unit configured to receive reflected echo signals from the object; a processor configured to act as a 3-dimensional elastic image constructing unit configured to construct a 3-dimensional elastic image by performing volume rendering on elastic volume data formed by elasticity values based on the reflected echo signals;
a processor configured to act as a 3-dimensional elastic image constructing unit configured to construct a 3-dimensional elastic image by performing volume rendering on elastic volume data formed by elasticity values based on the reflected echo signals;
the processor further configured to act as a cumulative opacity analyzing section configured to analyze a cumulative opacity with respect to a distance of a line of sight for each line-of-sight direction of the elastic volume data on which the volume rendering is performed and determine an optimal cumulative opacity for each line-of-sight direction based on the analysis,
the processor further configured to act as an elastic opacity table creating section configured to create an elastic opacity table and configured to set an opacity of a region other than a region of interest in the elastic opacity table for each line-of-sight direction based on the optimal cumulative opacity determined for each line-of-sight direction, so that the region of interest will not be hidden by the region other than the region of interest in the 3-dimensional elastic image; and
a display configured to display the 3-dimensional elastic image;
wherein
the 3-dimensional elastic image constructing unit is configured to, based on the elasticity values, set an opacity of the 3-dimensional elastic image using the elastic opacity table, wherein in the elastic opacity table a relationship between an opacity value and an elasticity value is set.

15. The ultrasonic diagnostic apparatus according to claim 14, wherein the elastic opacity table creating section is configured to set the opacity so that the region of interest has an opacity higher than the opacity of the region other than the region of interest.

16. The ultrasonic diagnostic apparatus according to claim 14, further comprising a 3-dimensional tomographic image constructing unit configured to generate tomographic volume data based on the reflected echo signals and perform volume rendering based on a luminance and an opacity of the tomographic volume data, wherein the display unit is further configured to display a 3-dimensional tomographic image.

17. A method for displaying an ultrasonic image, comprising:
performing, by an image processor, volume rendering on elastic volume data formed by elasticity values based on reflected echo signals of ultrasonic waves to display a 3-dimensional elastic image comprising a region of interest and a region other than the region of interest;
creating, by the image processor, an elastic opacity table setting a relationship between an opacity in the volume rendering of the elastic volume data and an elasticity value, the region of interest having a first opacity corresponding to a first elasticity value range in the elastic opacity table, and the region other than the region of interest having a second opacity corresponding to a second elasticity value range in the elastic opacity table, the second elasticity value range being a larger range than the first elasticity value range, the elastic opacity table setting the first opacity of the region of interest higher than the second opacity of the region other than the region of interest;

changing, by the image processor, the second opacity to a third opacity corresponding to the second elasticity value range in the elastic opacity table responsive to an operation by an operator on an opacity setting area;

setting, by the image processor, an opacity of the 3-dimensional elastic image depicting the region of interest and the region other than the region of interest using the elastic opacity table; and displaying, by a display, at least one of the 3-dimensional elastic image and the opacity setting area for setting an opacity of a region other than a region of interest relative to the first opacity of the region of interest in accordance with operation by the operator.

18. A method for displaying an ultrasonic image, comprising:

performing, by an image processor, volume rendering on elastic volume data formed by elasticity values based on reflected echo signals of ultrasonic waves to display a 3-dimensional elastic image comprising a region of interest and a region other than the region of interest;

selecting, by the image processor, one of a plurality of tables that are stored in advance, each of the plurality of tables setting a different predetermined relationship between an opacity in the volume rendering of the elastic volume data and an elasticity value, wherein the selected one of the plurality of tables serves as an elastic opacity table used to set an opacity of the region other than the region of interest relative to an opacity of the region of interest according to an operator selection of the one of the plurality of tables in an opacity table setting area, wherein the elastic opacity table sets the opacity of the region of interest higher than the opacity of the region other than the region of interest;

setting, by the image processor, an opacity of the 3-dimensional elastic image depicting the region of interest and the region other than the region of interest using the elastic opacity table; and displaying, by a display, the 3-dimensional elastic image and the opacity table setting area.

19. A method for displaying an ultrasonic image, comprising:

performing, by an image processor, volume rendering on elastic volume data formed by elasticity values based on reflected echo signals of ultrasonic waves to construct a 3-dimensional elastic image, wherein constructing the 3-dimensional elastic image comprises:

counting, by the image processor, a total number of voxels corresponding to a length of a line of sight within a region on which the volume rendering is performed for each line-of-sight direction of the elastic volume data on which the volume rendering is performed;

creating, by the image processor, an elastic opacity table and setting an opacity with respect to a region other than a region of interest in the elastic opacity table according to an inverse relationship with the total number of voxels counted for each line-of-sight direction, wherein the opacity with respect to the region other than the region of interest is decreased as the total number of voxels counted for each line-of-sight direction increases, and the opacity with respect to the region other than the region of interest is increased as the total number of voxels counted for each line-of-sight direction decreases; and constructing, by the image processor, the 3-dimensional elastic image by setting an opacity using the elastic opacity table based on the elasticity values; and displaying the 3-dimensional elastic image.

20. A method for displaying an ultrasonic image, comprising:

performing, by an image processor, volume rendering on elastic volume data formed by elasticity values based on reflected echo signals of ultrasonic waves to construct a 3-dimensional elastic image, wherein constructing the 3-dimensional elastic image comprises:

executing, by the image processor, processing for searching for a structural object on a line of sight, and counting a number of voxels up to the structural object, the total number of voxels corresponding to the length of a line extending up to the structural object;

creating, by the image processor, an elastic opacity table and setting an opacity according to the elastic opacity table, the elastic opacity table being configured to set an opacity with respect to a region other than a region of interest according to an inverse relationship with the total number of voxels counted for each line-of-sight direction, wherein the opacity with respect to the region other than the region of interest is decreased as the total number of voxels counted for each line-of-sight direction increases, and the opacity with respect to the region other than the region of interest is increased as the total number of voxels counted for each line-of-sight direction decreases;

and constructing, by the image processor, the 3-dimensional elastic image by setting an opacity using the elastic opacity table based on the elasticity values; and displaying the 3-dimensional elastic image.

21. A method for displaying an ultrasonic image, comprising:

performing, by an image processor, volume rendering on elastic volume data formed by elasticity values based on reflected echo signals of ultrasonic waves to construct a 3-dimensional elastic image, wherein constructing the 3-dimensional elastic image comprises:

analyzing, by the image processor, a cumulative opacity with respect to a distance of a line of sight for each line-of-sight direction of the elastic volume data on which the volume rendering is performed and determining an optimal cumulative opacity for each line-of-sight direction based on the analyzing;

setting, by the image processor, an opacity of a region other than a region of interest for each line-of-sight direction based on the optimal cumulative opacity determined for each line-of-sight direction, so that the region of interest will not be hidden by the region other than the region of interest in the 3-dimensional elastic image, in an elastic opacity table in which a relationship between an opacity in the volume rendering of the elastic volume data and an elasticity value is set; and constructing, by the image processor, the 3-dimensional elastic image by setting an opacity using the elastic opacity table based on the elasticity values; and displaying the 3-dimensional elastic image.

* * * * *